US009636212B2

(12) United States Patent
Tiedtke et al.

(10) Patent No.: US 9,636,212 B2
(45) Date of Patent: May 2, 2017

(54) DEVICE FOR REVERSIBLY ATTACHING AN IMPLANT IN AN EYE

(75) Inventors: Hans-Jürgen Tiedtke, Bonn (DE); Alexander Meyer, Bonn (DE)

(73) Assignee: PIXIUM VISION SA, Paris (FR)

( * ) Notice: Subject to any disclaimer, the term of this patent is extended or adjusted under 35 U.S.C. 154(b) by 1516 days.

(21) Appl. No.: 12/293,788

(22) PCT Filed: Jan. 26, 2007

(86) PCT No.: PCT/EP2007/000684
§ 371 (c)(1),
(2), (4) Date: Nov. 10, 2010

(87) PCT Pub. No.: WO2007/118526
PCT Pub. Date: Oct. 25, 2007

(65) Prior Publication Data
US 2011/0071627 A1   Mar. 24, 2011

(30) Foreign Application Priority Data
Mar. 31, 2006   (DE) .................. 10 2006 015 113

(51) Int. Cl.
*A61F 2/14* (2006.01)
*A61F 9/007* (2006.01)
*A61N 1/05* (2006.01)

(52) U.S. Cl.
CPC ................ *A61F 2/148* (2013.01); *A61F 2/14* (2013.01); *A61F 9/007* (2013.01); *A61F 2220/0008* (2013.01); *A61N 1/0543* (2013.01)

(58) Field of Classification Search
CPC .......... A61F 2/14; A61F 2/147; A61F 9/0017; A61F 9/00781; A61F 9/007; A61F 9/00727; A61F 2220/00–2220/0033
(Continued)

(56) References Cited

U.S. PATENT DOCUMENTS 4,060,089 A * 11/1977 Noiles .......................... 606/220
4,586,929 A    5/1986 Binder
(Continued)

FOREIGN PATENT DOCUMENTS

EP    0 138 564 B1    4/1985
JP    4130589 B2    5/2008
(Continued)

OTHER PUBLICATIONS

PCT International Preliminary Report on Patentability relating to International Application No. PCT/EP2007/000684, date of issuance of this report Nov. 17, 2008 (1 pg.).
(Continued)

*Primary Examiner* — Paul Prebilic
(74) *Attorney, Agent, or Firm* — Workman Nydegger

(57) ABSTRACT

The object of providing a device for reversibly attaching an implant to an eye, with which the implant can be attached in a simple way to the eye and can if necessary be detached or removed from the eye, is achieved according to the present invention by means of a device for attaching an implant by means of a pin that comprises a substantially elongated shaft, wherein the implant includes an implant film for contacting living tissue or nerves in the visual system of the eye and the implant film has an opening through which the shaft of the pin can be at least partially inserted, characterised in that the device includes a holding element that can be arranged on the shaft of the pin so that the holding element engages on the shaft of the pin and is fixed in an attachment position to the pin. By means of the device according to the invention the implant is on the one hand reliably attached, but can if necessary be detached from the retina by removing the holding element or retainer, wherein the pin anchored in the eye does not have to be removed at the same time, but can be re-used. Damage or injury to the tissue of the eye that
(Continued)

Figure 1:
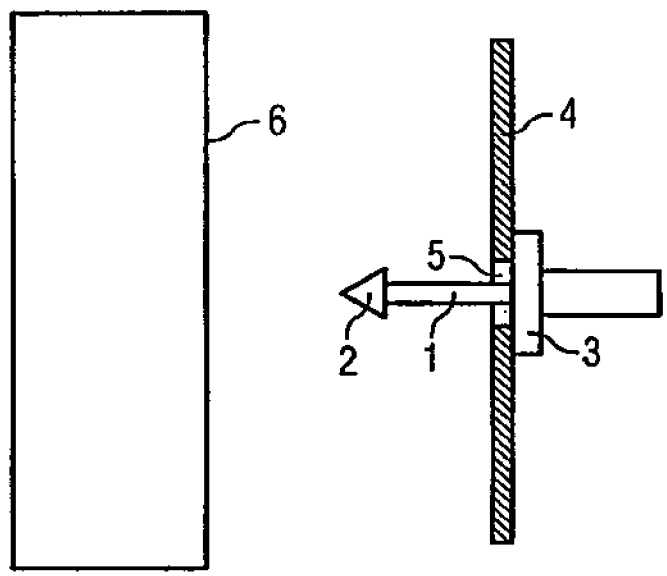

would otherwise be associated with the removal of the pin can thereby also be avoided.

35 Claims, 7 Drawing Sheets

(58) Field of Classification Search
USPC .............. 606/219, 220, 155, 75, 329, 139; 623/4.1, 5.11, 5.15, 6.12, 6.63; 411/508
See application file for complete search history.

(56) References Cited

U.S. PATENT DOCUMENTS

| | | | |
|---|---|---|---|
| 4,784,126 A * | 11/1988 | Hourahane | 606/60 |
| 4,793,335 A * | 12/1988 | Frey et al. | 623/13.14 |
| 4,994,073 A * | 2/1991 | Green | 606/220 |
| 5,441,502 A * | 8/1995 | Bartlett | 606/104 |
| 5,725,261 A * | 3/1998 | Rahn | 292/307 R |
| RE36,289 E * | 8/1999 | Le et al. | 606/232 |
| 5,935,155 A | 8/1999 | Humayun et al. | |
| 6,551,291 B1 * | 4/2003 | de Juan et al. | 604/294 |
| 2003/0069603 A1 | 4/2003 | Little et al. | |
| 2004/0078064 A1 | 4/2004 | Suzuki | |
| 2006/0015105 A1 * | 1/2006 | Warren et al. | 606/72 |

FOREIGN PATENT DOCUMENTS

| | | |
|---|---|---|
| JP | 2009-501873 | 1/2011 |
| WO | WO 03/039661 A1 | 5/2003 |
| WO | WO 2004/112893 A2 | 12/2004 |

OTHER PUBLICATIONS

PCT English Translation of the Written Opinion of the International Searching Authority relating to International Application No. PCT/EP2007/000684 (9 pgs.).

International Search Report for International Application No. PCT/EP2007/000684 and English translation thereof; date of mailing May 31, 2007 (10 pages).

Written Opinion for International Application No. PCT/EP2007/000684; dated Jan. 26, 2007; 8 pages.

* cited by examiner

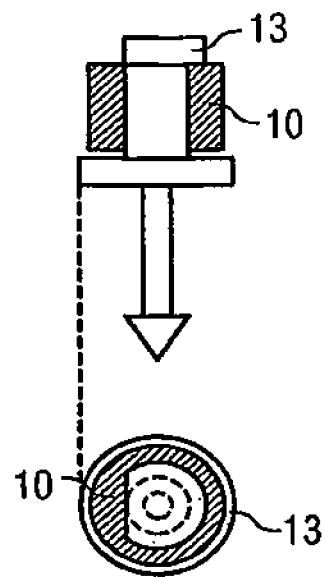
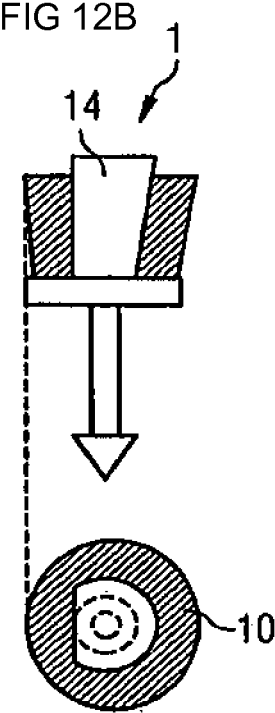
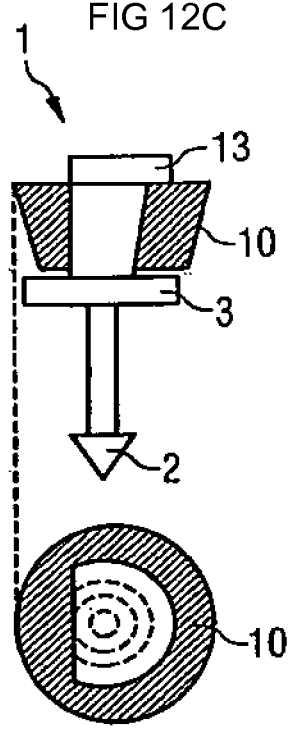
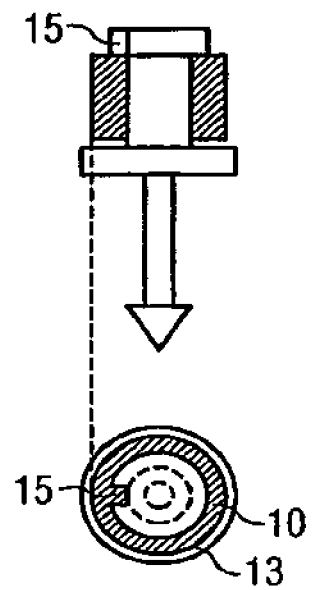
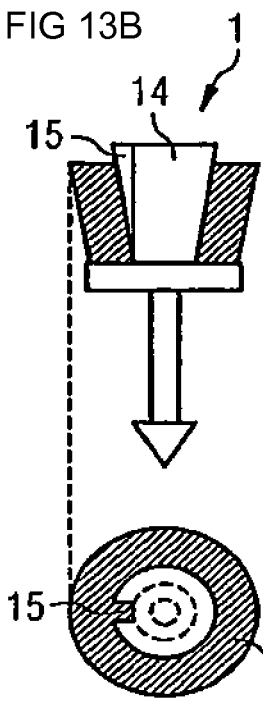
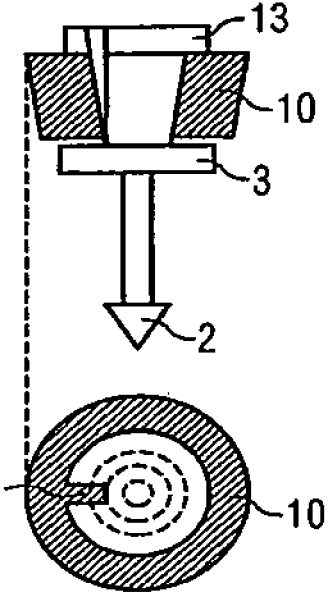

DEVICE FOR REVERSIBLY ATTACHING AN IMPLANT IN AN EYE

This application is the national stage of PCT/EP2007/000684 filed Jan. 26, 2007, which claims priority to DE 10 2006 015 113.5 filed Mar. 31, 2006, both of which are hereby incorporated by reference in their entirety.

The present invention relates to a device for reversibly attaching an implant to the eye or in the eye of a human or a mammal. The present invention relates to a device for reversibly attaching an implant, as well as to a tool for applying the device according to the invention.

A common cause of partial or complete loss of sight is the destruction of the photoreceptor layer in the retina of the human eye, as a result of which incident photons are not converted into corresponding stimuli of the ganglion cells. In this clinical picture the ganglion cells are only partially affected, so that an external stimulation of the ganglion cells still present in the retina can generate a visual perception. On this basis, developments have been carried out for some time, which involve the implantation of a micro-contact structure with stimulation electrodes for contacting intact ganglion cells.

Devices are known in the form of passive or active implants for the retina of the human eye, which are intended for the treatment of patients whose sight has been partially or completely lost due to defects in the retina. With active implants the image detected by an external camera is in principle converted into electrical signals and is transmitted via the stimulation electrodes of the micro-contact structure by means of electrical stimulation pulses to the ganglion cells of the retina or to the optic nerve, in order thereby to restore or improve the sight of the blind or partially blind patient.

Such micro-contact structures essentially consist of an implant film that carries electrically conducting, stud-shaped or pin-shaped contact elements that are uniformly distributed over the surface of the implant film and project above the plane of the implant film, so as to contact the ganglion cells of the retina. In order to ensure a good functionality of such implants the implant films have to be reliably fixed to the retina and/or to the sclera of the eye.

The attachment of a passive or active implant in the eye of a human or a mammal is carried out according to the prior art using pins or tacks or by means of a selective in-growth. When a pin is used, the implant is placed on the retina or the implant is placed over the pin and, with the aid of a special forceps, the pin is then drilled into the retina and sclera of the eye, where it becomes permanently anchored in the relatively thick sclera due to its barbs.

Figure 2:
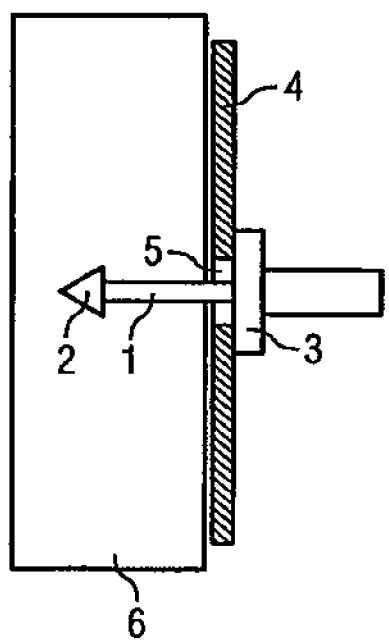

The FIGS. 1 and 2 show the procedure according to the prior art for implanting an implant inside an eye. In FIG. 1 an implant is illustrated before its attachment in the eye, wherein the implant includes an implant film that is to be fixed to the retina/sclera of an eye by means of a pin according to the prior art. The pin has barbs at its tip and is provided in the region of its middle portion with a collar, which has a larger diameter than the remaining body of the pin. The implant film has an opening which is dimensioned so that the pin can be inserted there-through, but is of smaller diameter than the collar of the pin. For the attachment of the implant film to the retina/sclera of the eye, the pin is inserted so far into the opening in the implant film until the collar of the pin rests against the implant film.

In FIG. 2 the implant shown in FIG. 1 is illustrated after the attachment to the retina/sclera of the eye by means of the pin according to the prior art. In this attached state the implant film of the implant is fixed to the retina/sclera of the eye by the pin, whereby the pin is drilled into the tissue of the retina/sclera and anchored therein by means of its barbs. As the collar has a larger diameter than the opening in the implant film, the collar of the pin forms a stop means that holds the implant film in its position on the retina/sclera of the eye.

With this attachment procedure according to the prior art the implant can no longer be removed or detached from the eye without removing the pin. When removing the pin, however, part of the retina is irreversibly destroyed due to the pin's barbs, which can lead to detachment of the retina. Further, with the above-described attachment method the problem exists that pin and implant have to be inserted together and thus have to be manipulated simultaneously in the interior of the eye, which greatly increases the danger of damaging the retina due to unintentional contact of the latter by parts of the implant or pin. In addition, the implant can easily be damaged due to the sharp barbs of the pin.

In another known attachment method, which is still in the development phase, the attachment of implants in the interior of an eye is effected with adhesives, in which fibrin-like adhesives are used. These adhesives have the disadvantage, however, that they do not produce an immediate attachment, but only cure after a relatively long time, which means that in the meantime the implant additionally has to be affixed by means of another method. Furthermore, these adhesives can increase the danger of cell excrescence(proliferation) in the eye.

An object of the present invention is consequently to provide a device for reversibly attaching an implant in an eye, by means of which the implant can be attached in a simple way in the eye or to the eye and can, if necessary, be detached and removed from the eye, whereby damage or injury to the tissue of the eye is reduced to a minimum.

The present invention achieves the object mentioned above by a device for attaching an implant to the eye of a human or mammal by means of a pin which comprises a substantially elongated shaft, wherein the implant includes an implant film for contacting living tissue or nerves in the visual system of the eye, the implant film having an opening through which the shaft of the pin can be at least partly inserted, characterised in that the device includes a holding element that can be arranged on the shaft of the pin such that the holding element grips on the shaft of the pin and is fixed in an attachment position on the pin.

The present invention provides a reversible and as far as possible damage-free attachment of an implant to the eye and in particular to the retina of an eye. By means of the device according to the invention, the implant is on the one hand reliably attached to the retina, though the implant can if necessary be detached from the retina by removing the holding element or retainer. The holding element can be detached in a simple manner, for example, by using tweezers or a scalpel and can be removed from the pin. The pin or tack can remain in the ocular tissue of the patient and can thus be re-used in a further implanting procedure. As the pin does not have to be removed when extracting an implant from the eye, damage or injury to the tissue of the eye, which would otherwise be associated with the removal of the pin, can also be avoided. This is particularly advantageous if the pin is anchored in the sensitive retina and/or sclera of the eye for the attachment of an implant.

According to a preferred embodiment of the device according to the invention the pin comprises a shaft of substantially elongated shape and of circular cross-section. A collar is formed in the central region of the shaft, which has a larger diameter than the shaft of the pin. According to a further preferred embodiment, on the side of the collar pointing towards the tip of the pin (front part of the pin) the shaft has a smaller diameter than on the other side of the collar (rear part of the pin). As a result, the front part of the pin with its smaller diameter is able to be placed in the tissue more easily and with as little as possible damage to the tissue, while the rear part of the pin with its larger diameter offers a better attachment piece for the arrangement and attachment of the implant. The pin is provided at its tip with at least one barb, so that the body of the pin corresponds substantially to the shape of an arrow, in the middle region of which a plate-shaped collar is formed.

The implant film of the implant to be attached has an opening, which can be in the form of a hole, slot, notch or some other suitable recess. The opening in the implant film is dimensioned so that the implant film can be mounted on the shaft of the pin, in that the shaft of the pin is inserted with its rear part through the opening in the implant film as far as the collar. The opening in the implant film, however, has a smaller diameter than the collar of the pin. On account of this dimensioning of the opening in the implant film, the diameter of the shaft of the pin, and the diameter of the collar of the pin, the opening in the implant film can be guided on the rear part of the shaft of the pin until the implant film rests against the collar of the pin.

For attaching an implant in the interior of an eye by means of the device according to the present invention, the pin with the tip and its front part is firstly bored into the tissue or the retina/sclera of the eye until the collar of the pin rests on the tissue. On account of the barbs on the tip of the pin, the latter remains firmly anchored in the tissue. With the device according to the invention an implant may, however, also be attached outside of the eyeball, for example on the sclera of the eye. After the placement of the pin in the tissue to which the implant is to be attached, the implant or the implant film itself can be arranged on the pin. This is carried out in that the implant is mounted onto the rear part of the pin or the part opposite the tip of the pin anchored in the tissue, whereby the rear part of the shaft of the pin is inserted into the opening in the implant film until the implant film abuts the collar of the pin.

The holding element is then placed immediately behind the implant film on the rear part of the shaft of the pin. The dimensions of the holding element are configured such that the holding element does not pass through the opening in the implant film, but rather rests on the rear side of the implant film. The holding element is attached on the rear part of the shaft of the pin on the rear side of the implant film facing away from the tissue, preferably immediately behind the implant film. In this way the implant film of the implant is fixed on the retina/sclera of the eye by the pin anchored in the tissue and the holding element attached to the pin.

The holding element preferably exerts an independent clamping action, so that it is independently fixed after it has been placed in the desired position on the shaft of the pin. For this purpose the holding element can for example be designed as a rubber ring, which in the state attached to the shaft of the pin has larger dimensions than the opening in the implant film and thus holds the implant film on the shaft of the pin. If the rubber ring in the unstressed state has a smaller diameter than the rear part of the shaft of the pin, the rubber ring exerts a tensile stress and thus a pressing force when it is slid onto the shaft of the pin, so that in the attached state after it has been placed on the shaft of the pin it is independently fixed and thereby holds the implant film in the desired position. In this way, the implant or implant film is attached to the pin in such a way that it cannot become detached due to eye movements or accelerations that occur for example during daily use by the implant-wearer.

The holding element can also be designed as a clamping spring, which does not have to completely surround the shaft of the pin in the attached state, but encompasses it at least partially. This holding element designed as a clamping spring is advantageously provided with a pre-tension, so that the holding element is fixed with its intrinsic elastic force in the attached state on the shaft and thus holds the implant film in the desired position. The configuration of the holding element as a rubber ring or clamping spring furthermore has the advantage that the holding element, due to expansion against the spring force or against the tensile force or pressing force of the rubber, can be removed again from the shaft of the pin as required, in order for example to extract the implant or to re-position the holding element.

Figure 3:
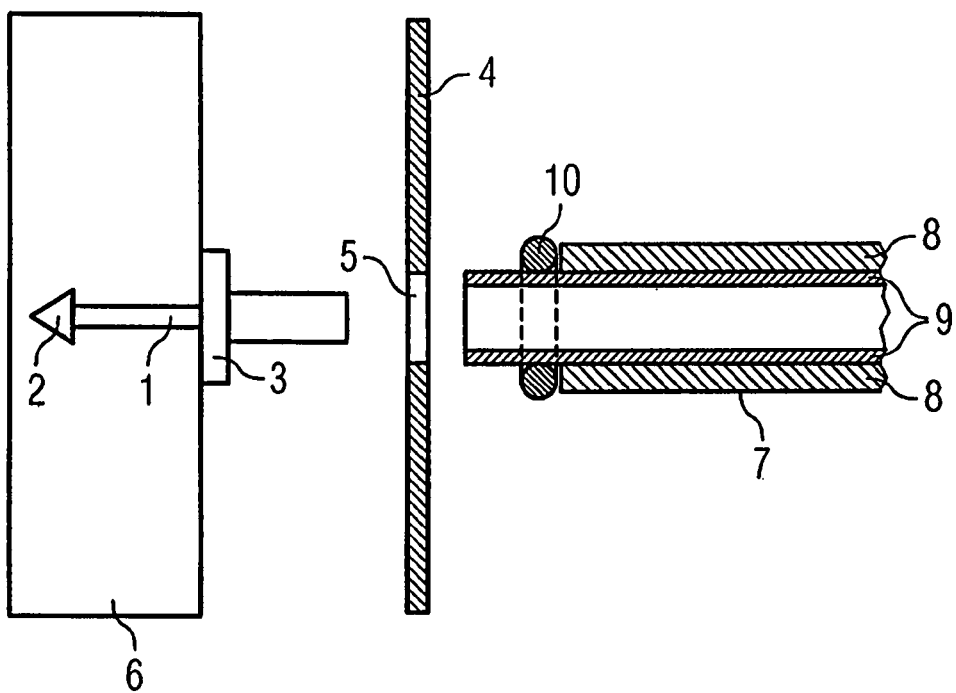
Figure 4:
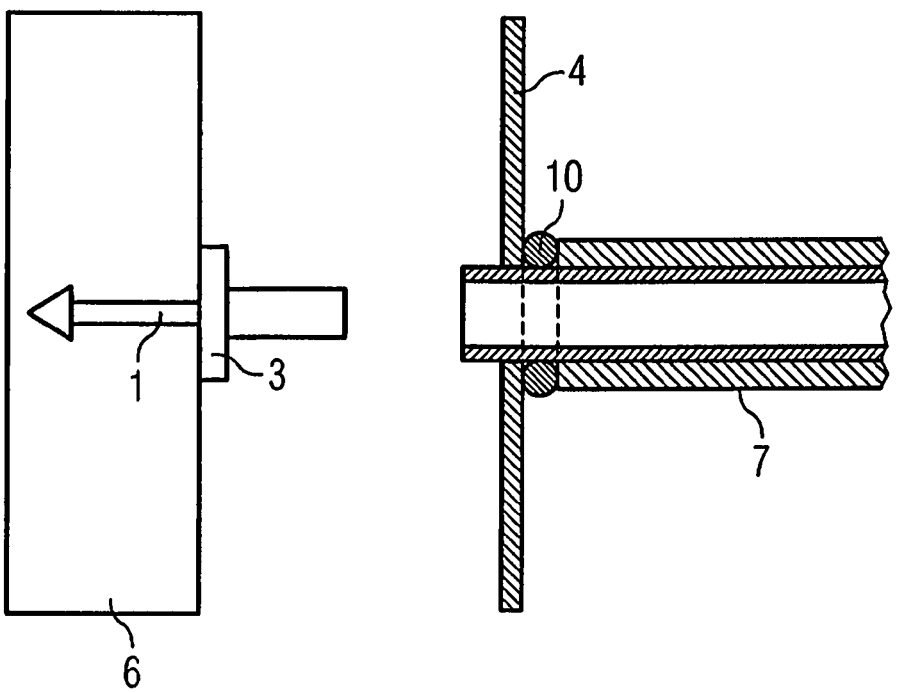
Figure 5:
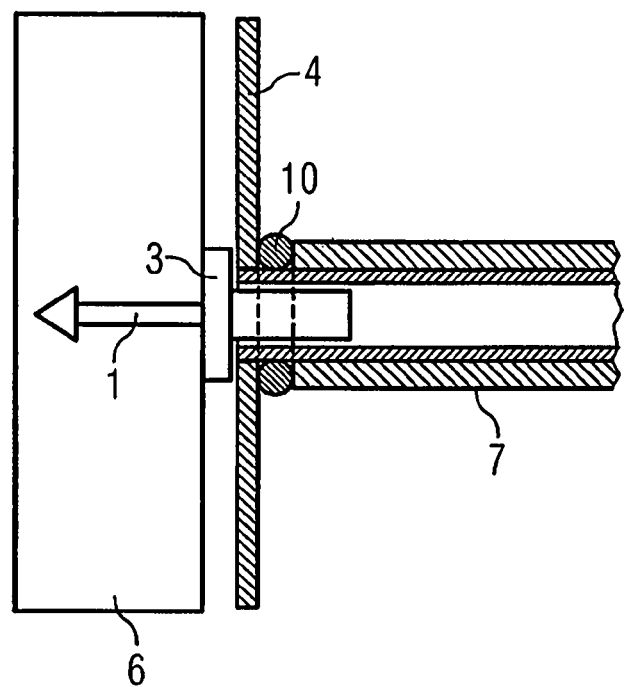
Figure 6:
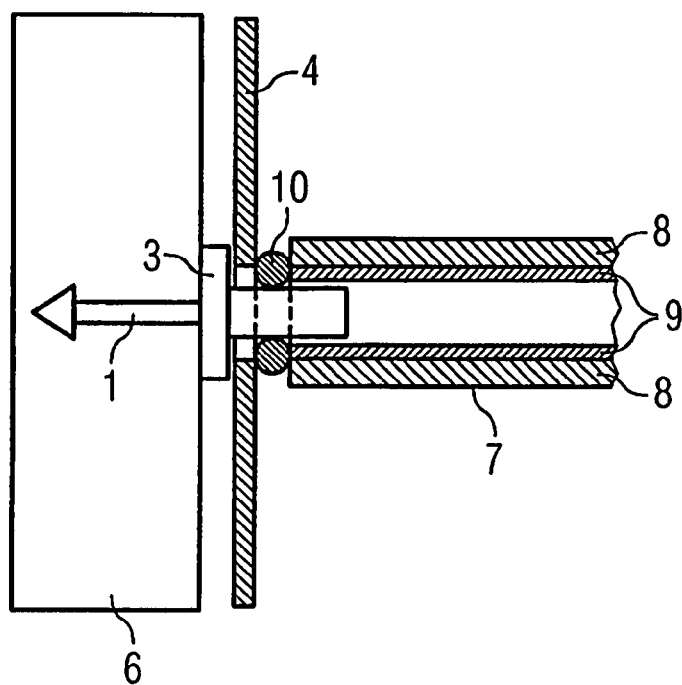
Figure 7:
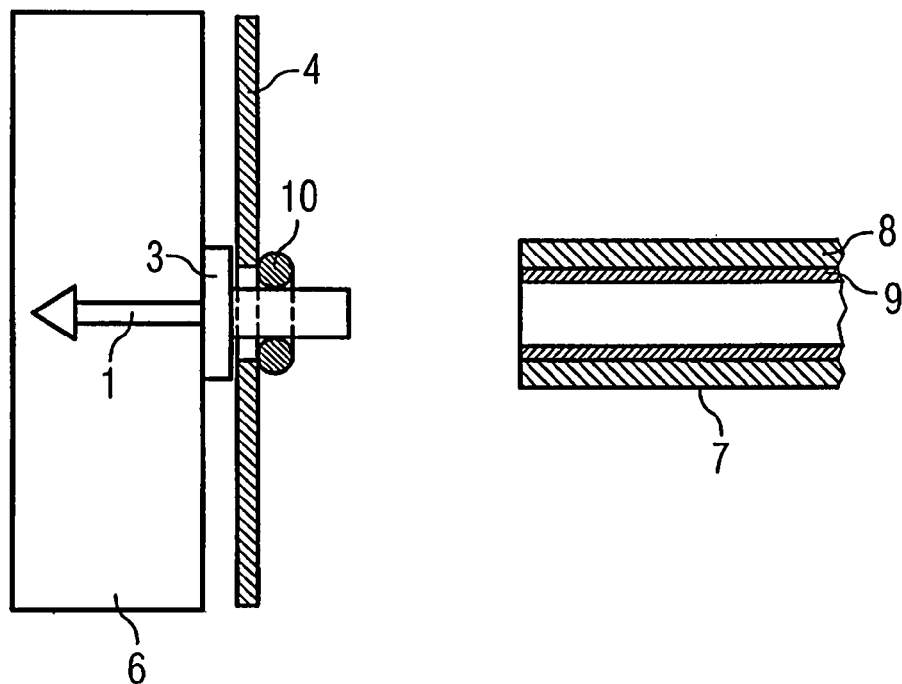
Figure 8:
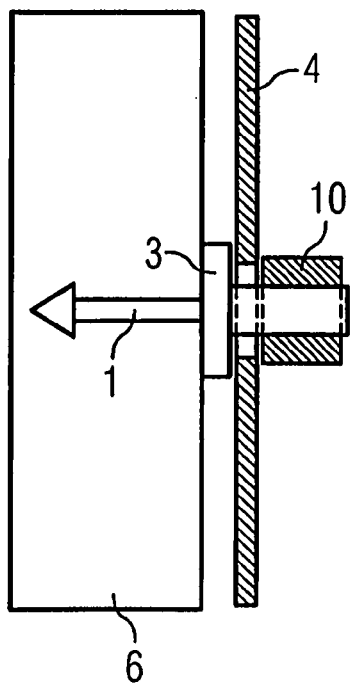
Figure 9:
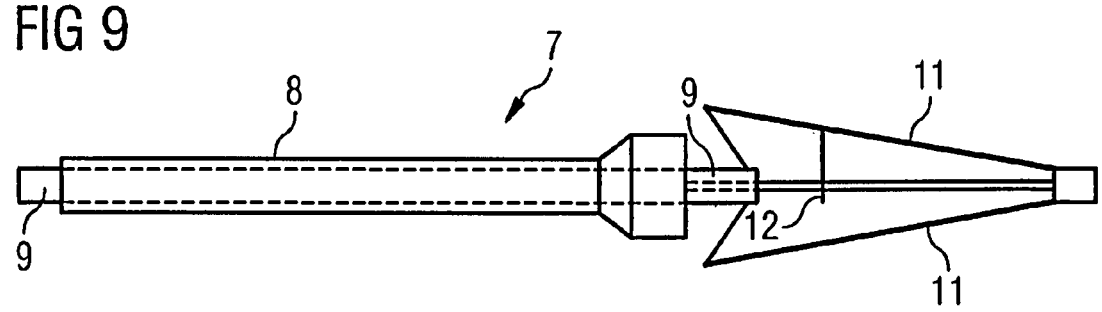
Figure 10A:
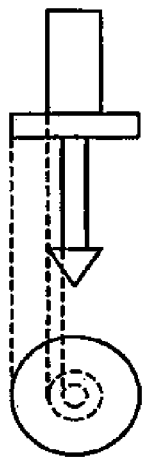
Figure 10B:
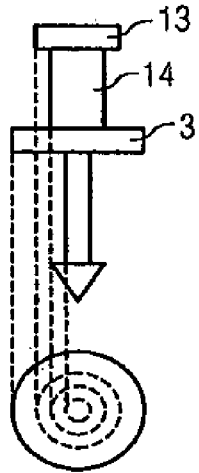
Figure 10C:
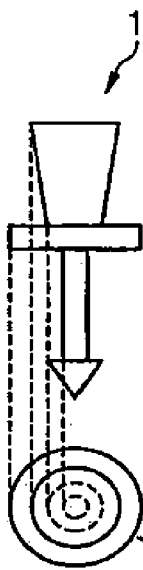
Figure 10D:
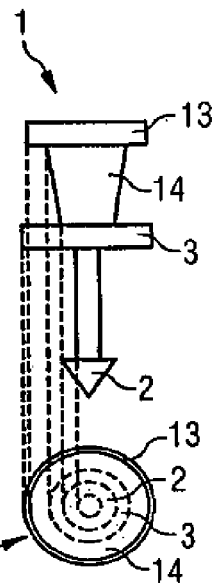
Figure 11A:
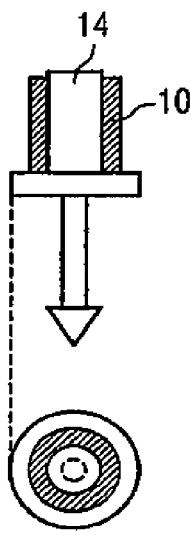
Figure 11B:
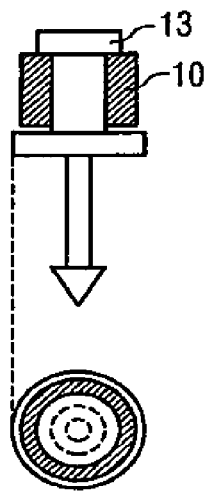
Figure 11C:
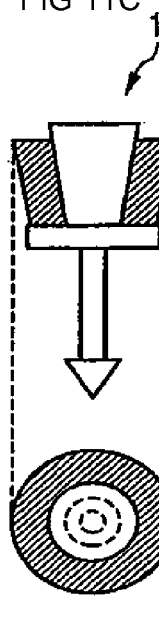
Figure 11D:
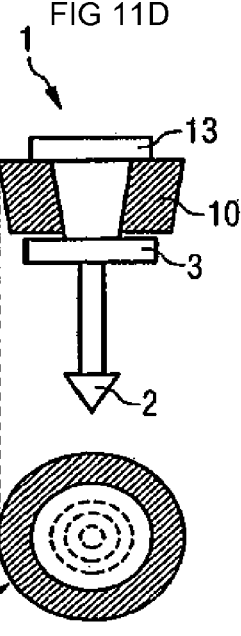

Further details, preferred embodiments and advantages of the present invention follow from the following description given with reference to the accompanying drawings. They show:

FIG. 1 the schematic representation of a preparatory stage in the procedure described above for attaching an implant by means of an attachment device according to the prior art in the interior of an eye;

FIG. 2 the schematic representation of the implant illustrated in FIG. 1 in the attached state, which is attached in the interior of an eye by means of the attachment device described above according to the prior art;

FIG. 3 the schematic representation of a first stage in the procedure for attaching an implant in the interior of an eye by means of an attachment device according to a preferred embodiment of the present invention;

FIG. 4 the schematic representation of a second stage in the procedure for attaching an implant in the interior of an eye by means of an attachment device according to a preferred embodiment of the present invention;

FIG. 5 the schematic representation of a third stage in the procedure for attaching an implant in the interior of an eye by means of an attachment device according to a preferred embodiment of the present invention;

FIG. 6 the schematic representation of a fourth stage in the procedure for attaching an implant in the interior of an eye by means of an attachment device according to a preferred embodiment of the present invention;

FIG. 7 the schematic representation of a fifth stage in the procedure for attaching an implant in the interior of an eye by means of an attachment device according to a preferred embodiment of the present invention;

FIG. 8 the schematic representation of an implant that has been attached in the interior of an eye by means of a device according to a further preferred embodiment of the present invention;

FIG. 9 the schematic representation of a tool for manipulating an attachment device according to a preferred embodiment of the present invention; and FIGS. 10A-10D, 11A-11D, 12A-12C, and 13A-13C show several representations of a number of pins in various embodiments such as can be used in a device according to the invention for attaching an implant to an eye.

In the following section a preferred embodiment of the present invention is described with a procedure showing how the implantation and attachment of an implant in the eye is carried out by means of the device according to the invention with the aid of a special tool.

FIGS. 3 to 8 show in each case schematic representations of a section of the retina/sclera 6 of a treated eye, on which an implant is attached. In the first stage of the procedure for attaching an implant in the interior of an eye by means of the device according to the invention shown in FIG. 3, a pin or tack 1 is already anchored in the retina and/or sclera 6 of the treated eye, wherein the pin 1 was before-hand inserted with its front end completely in the retina/sclera 6 without the implant and is anchored with the barbs on the tip in the retina/sclera 6 of the eye. The implant or the implant film 4 is not involved in the procedure for inserting and anchoring the pin 1. This has the advantage that the pin 1 can firstly be placed very precisely without the implant 4, since the implant 4 is not yet located in the eye and does not have to be manipulated together with the pin 1 in the constricted space of the interior of the eye and under the conditions of limited visibility.

In the situation illustrated in FIG. 3, the implant film 4 is located between the retina/sclera 6 and the special tool 7, which basically consists of two tubes 8 and 9 displaceably guided in one another. As can be seen in FIG. 3, the inner tube 9 projects at the front side directed to the implant film by a specific length beyond the outer tube 8 or from the outer tube 8 of the tool 7. A holding element in the form of a rubber ring 10 of elastic material (for example silicone) is fitted over the protruding part of the inner tube 8, and surrounds the inner tube 9 and at the same time rests on the front surface of the outer tube 8 of the tool 7.

The implant film 4 has an opening 5, the diameter of which is larger than the diameter of the inner tube 9 but is smaller than the diameter of the outer tube 8. In the second stage of the attachment procedure illustrated in FIG. 4, the opening 5 of the implant film 4 is placed over the inner tube 9 of the tool 7, the inner tube previously having been inserted into the opening 5 in the implant film 4. The tool 7 and implant film 4 connected to one another in this way are brought up to the pin 1 anchored in the retina/sclera 6. In a variant of the procedure for attaching an implant in the inside of an eye by means of the device according to the invention the implant film 4 is not placed on the tool 7, but instead the implant film 4 is firstly placed on the rear part of the pin 1 projecting from the retina/sclera 6, wherein the shaft of the pin 1 is guided into the opening 5 of the implant film 4. The tool 7 is then used to fix the implant film 4 on the pin 1, which procedure is described hereinafter.

In the third stage of the attachment procedure illustrated in FIG. 5, the tool 7 together with the implant film 4 is mounted on the rear part of the pin 1. The diameter of the inner tube 9 is dimensioned so that it can receive the rear part of the pin 1. In this way the tool 7 can be placed on the rear part of the pin 1 and advanced on the shaft of the pin 1 until it comes into contact with the collar 3 of the pin 1. In this connection the tool 7 is displaced on the shaft of the pin 1 until the inner tube 9 of the tool 7 comes into contact with the collar 3 of the pin 1.

The implant film 4 mounted on the shaft of the pin 1 anchored in the retina/sclera 6 is then fixed in position, which is effected by means of the holding element or rubber ring 10. In the fourth stage of the attachment procedure illustrated in FIG. 6, the tool 7 is still mounted on the rear part of the pin 1, but the inner tube 9 is retracted into the outer tube 8, so that the front faces of the two tubes 8, 9 are flush with one another. On retracting the inner tube 9 into the outer tube 8 the rubber ring 10 is held in its position and is stripped from the inner tube 9 by the outer tube with the larger diameter. The rubber ring 10 thus now sits directly on the shaft of the pin 1. On account of the pre-tensioning of the elastic material the rubber ring 10 has contracted around the shaft of the pin 1.

Following this, the tool 7 can be removed, as illustrated in FIG. 7. The rubber ring 10 develops a fastening action through its tensile force and pressing force and the static friction between the rubber ring 10 and the shaft of the pin 1, whereby the rubber ring 10 is "secured" on the shaft of the pin 1. As the rubber ring 10 also in the contracted state has a larger diameter than the opening 5 in the implant film 4, the implant film 4 is fixed in its position on the shaft of the pin 1 by the rubber ring 10.

Alternatively, the attachment of the implant to the shaft of the pin can also be carried out with the aid of a clamping device, which at least partly surrounds the shaft of the pin 1. Furthermore the attachment of the implant to the shaft of the pin can also be carried out with a split-pin, for example made of polyimide, which is inserted in a depression or notch in the shaft of the pin, or with a screw that engages on a thread of the pin.

FIG. 8 schematically shows an implant that has been attached to the inside of an eye by means of a device according to a further preferred embodiment of the present invention, wherein only the final stage in the attached state is shown. In contrast to the embodiment described above, with this further embodiment the rubber ring 10 is shaped not as a torus but as a sleeve. With this configuration the rubber ring 10 can surround the shaft of the pin 1 in the manner of a sheath. In this way the static friction between the rubber ring 10 and the shaft of the pin 1 is increased on account of the larger contact area, which improves the securing action of the rubber ring 10 and thus the fixing of the implant film 4.

FIGS. 10A, 10B, 10C, 10D, 11A, 11B, 11C, 11D, 12A, 12B, 12C, 13A, 13B and 13C (also referred to herein as FIGS. 10 to 13) show several representations of pins and tacks in various embodiments, such as can be employed in a device according to the invention for attaching an implant to an eye. In this connection, the pins 1 in the upper part of FIGS. 10 to 13 are shown in each case in a side view, and in the lower part of the figures in cross-section Q. Whereas in FIG. 10 the pins 1 are in each case shown without a holding element 10, FIGS. 11 to 13 show the pins 1 together with a holding element 10 arranged thereon.

In two of the embodiments illustrated in FIGS. 10 and 11 the rear region of the pin 1 has a conically shaped region 14, the diameter of which decreases progressively from the rear up to the collar 3 of the pin 1. In other embodiments the pin 1 is in each case provided with an under-cut 13, which has a larger diameter than the rear region of the pin 1 and also has a larger diameter than the conically shaped region 14. The diameters of the individual elements of the pin 1 are shown in the cross-sections Q of the relevant embodiments.

In FIG. 11, the embodiments of the pins and tacks 1 shown in FIG. 10 are illustrated together with the holding elements 10 arranged thereon. It can be seen therein that the under-cut 13 forms a stop, which prevents a displacement of the holding elements 10. In the embodiments with the conically shaped region 14 it can be seen that the conical section on the shaft of the pin co-operates in each case with the holding element 10 and the holding element 10 is thereby urged in the direction of the tip 2 of the pin, until the said holding element 10 abuts on the collar 3 of the pin. An implant film in the attached state is thereby pressed in the direction of the tip 2 onto the collar 3 of the pin 1.

In the embodiments of the pins and tacks 1 illustrated in FIG. 12, the under-cut 13 is partly flattened on one side in order to facilitate the mounting of the holding element 10 on the shaft of the pin 1. In addition or alternatively, the conical region 14 can also be flattened on one side. In the embodiments of the pins and tacks 1 illustrated in FIG. 13, the under-cut 13 and/or the conical region 14 on the shaft of the pin 1 is provided with a notch 15, in which a groove on the inner circumference of the holding element 10 can engage in the attached state, in order to prevent a rotation of the holding element 10 on the shaft of the pin 1.

The implantation and attachment of an implant in the eye by means of the device according to the invention is preferably carried out with the aid of a special tool (retainer tool). FIG. 9 schematically shows a tool for manipulating an attachment device according to a preferred embodiment of the present invention. The tool 7 consists in this preferred embodiment of two tubes 8 and 9 inserted into one another and movable relative to one another, wherein in a first position the inner tube 9 projects at the front side partly from the outer tube 8. Since the inner tube 9 and the outer tube 8 are displaceable relative to one another, the inner tube 9 can be retracted with respect to the outer tube 8 and thus brought into a second position, in which the front side of the inner tube 9 no longer projects from the outer tube 8, but is aligned flush with the latter or the inner tube 9 is retracted into the outer tube 8.

Instead of the inner tube 9 and the outer tube 8, other arbitrarily shaped hollow bodies can also be used.

Important in this connection is that the hollow bodies used can be guided within one another and are movable relative to one another. As a further feature, the inner hollow body 9 should have a hollow section at least on its operative front side, with which the holding element 10 (and the implant film 4) is placed on the pin 1, so that the inner hollow body 9 can be fitted with its front side on the pin 1. It is also advantageous if the inner hollow body 9 has round external contours at least on its front side, so that the holding element 10 that is under pretension can easily be mounted thereon and removed there-from in order to place the holding element on the shaft of the pin 1, as described above.

On the side opposite the front side of the tubes 8 and 9 the tool 7 is provided with an actuating mechanism, with which the relative movement of the inner tube 9 with respect to the outer tube 8 can be produced. In the embodiment illustrated in FIG. 9, the actuating mechanism of the tool 7 includes two gripping elements 11, which are articulatedly mounted in a common end point and are each connected at their free end to the inner tube 9. When the gripping elements 11 are squeezed together, this operates the actuating mechanism so that the inner tube 9 is withdrawn from the outer tube 8 in the direction of the gripping element 11, i.e. the inner tube 9 on the front side facing opposite the gripping element 11 is retracted into the outer tube 8. The actuating mechanism of the tool 7 is furthermore provided with a mechanical stop 12, which limits the movement of the gripping elements 11. This mechanical stop 12 is preferably configured so that the gripping elements 11 can be squeezed until the front side of the inner tube 9 is completely retracted into the outer tube 8. In this connection the inner tube 9 is guided on a shaft that extends from the inner tube 9 up to the common end point of the gripping elements 11.

It is particularly advantageous if the gripping elements 11 are held in the open position by a pre-tensioning, in which the inner tube 9 at the front side projects from the outer tube 8. In this way the tool 7, together with the holding element 10 (and the positioned implant film 4) mounted on the projecting part of the inner tube 9, can be brought into position on the anchored pin 1, while the gripping elements 11 are reliably held in the open position due to the pre-tensioning (for example by means of a spring). Only when the tool 7 together with the holding element 10 and the positioned implant film 4 on the anchored pin 1 have been brought into the desired position, can the gripping elements 11 of the tool 7 be squeezed against the pre-tensioning and thereby operate the actuating mechanism, which on the front side of the tool 7 effects the retraction of the inner tube 9 into the outer tube 8. In this way, the holding element 10 is mounted on the shaft of the pin 1 and the implant film 4 is fixed in the desired position, as described above.

With an implant that is attached with the device according to the invention, the implant can be detached as required by firstly removing the holding element 10 from the shaft of the pin. This can occur by pulling off the holding element, for example with pincers. Alternatively, the holding element can be cut open, for example with a scalpel or another suitable tool, along the shaft of the pin and removed. Following this the implant 4 can be lifted off from the shaft of the pin 1, wherein the pin 1 anchored in the retina/sclera remains in the eye of the implant-wearer and can advantageously be used for a subsequent re-implantation.

LIST OF REFERENCE NUMERALS

1. Pin
2. Tip of the pin
3. Collar of the pin
4. Implant or implant film
5. Opening in the implant film
6. Retina/sclera of the eye
7. Tool
8. Outer tube of the tool
9. Inner tube of the tool
10. Holding element or rubber ring
11. Gripping element on the tool
12. Stop on the tool
13. Under-cut of the pin
14. Conical section on the shaft of the pin
15. Notch in the under-cut and/or in the shaft of the pin
Q Cross-section of the pin

The invention claimed is:
1. An implant attaching device for reversibly attaching an implant in an eye of a human or mammal, wherein the implant includes an implant film for contacting living tissue or nerves in a visual system of the eye and the implant film comprises an opening, the implant attaching device comprising two distinct elements:
(i) a pin configured to fix the implant to living tissue or nerves, wherein the pin comprises an elongated shaft having a rear part and a front part, wherein the front part includes a barb configured to anchor the elongated shaft in the living tissue or nerves; and
(ii) a holding element for holding the implant film in contact with living tissue or nerve wherein the holding element is configured to be disposed on the rear part of the elongated shaft, and to be removably arranged on the rear part of the elongated shaft, so that the holding element is configured to engage on the elongated shaft and to removably hold the implant film of the implant in an attachment position on the rear part of the elongated shaft of the pin,
wherein in an attached state of the pin, the holding element exerts an elastic force directed towards an axial center of the pin and is configured to be removably arranged on the elongated shaft of the pin, so that the holding element engages on the elongated shaft of the pin and is removably fixed on the pin, wherein the holding element has a thickness in a longitudinal direction of the elongated shaft that is less than a length of the elongated shaft, wherein dimensions of the rear part of the elongated shaft of the pin are such that the rear part of the elongated shaft of the pin can be inserted through the opening of the implant film, wherein in the attached state, the rear part of the elongated shaft passes through the opening of the implant film such that the implant film is positioned on the rear part of the elongated shaft and such that the holding element is positioned immediately behind the implant film on the rear part and such that the implant film is positioned between the holding element and the living tissue or nerves.

2. The device according to claim 1, wherein the holding element arranged on the shaft of the pin at least partially surrounds the shaft of the pin and co-operates mechanically with the shaft to fix the implant film placed on the shaft of the pin in the attached state on the pin.

3. The device according to claim 1, wherein the device for attaching an implant is designed so that the implant can be attached inside the eyeball on the retina and/or on the sclera of the eye.

4. The device according to claim 1, wherein the device for attaching an implant is designed so that the implant can be attached outside the eyeball to the sclera of the eye.

5. The device according to claim 1, wherein a collar is formed in a middle region of the shaft of the pin, and the collar has a larger diameter than the shaft of the pin.

6. The device according to claim 5, wherein the front part of the pin is on a first side of the collar and the rear part is on a second side of the collar, wherein the shaft on the first side of the collar has a smaller diameter than the shaft on the second side of the collar.

7. The device according to claim 1, wherein the shaft of the pin has at least one conical section in the region in which the holding element is arranged in the attached state.

8. The device according to claim 1, wherein the shaft of the pin has at least one under-cut, which limits a region in which the holding element is arranged in the attached position of the device.

9. The device according to claim 1, wherein the shaft of the pin has at least one depression or notch, in which the holding element at least partially engages in the attached state.

10. The device according to claim 1, wherein the pin is provided at its tip with at least one barb, with which the pin is anchored in the tissue in the attached position of the device.

11. The device according to claim 1, wherein the implant film of the implant to be attached has an opening that is dimensioned so that the implant film can be placed on the shaft of the pin, when the shaft of the pin is inserted through the opening in the implant film.

12. The device according to claim 1, wherein the dimensions of the holding element are such that the holding element in the attached position of the device does not pass through the opening in the implant film, but abuts at least partially on a rear side of the implant film facing away from the tissue.

13. The device according to claim 5, wherein the opening in the implant film has a smaller diameter than the collar of the pin.

14. The device according to claim 5, wherein the diameter of the shaft of the pin and the diameter of the collar of the pin and the opening in the implant film are dimensioned such that the opening in the implant film can be guided on the shaft of the pin until the implant film abuts against the collar of the pin.

15. The device according to claim 5, wherein, in the attached position of the device, the pin with the tip and a front part of the tip is configured to be bored into the tissue or into the retina/sclera of the eye and the collar of the pin is configured to rest on the tissue.

16. The device according to claim 1, wherein the holding element is releasable from the attached position of the device in order to release the attached implant from the shaft of the pin by expanding or opening the holding element.

17. The device according to claim 1, wherein the implant in the attached state on the retina/sclera of the eye is fixed in position by the pin that is configured to be anchored in the tissue and by the holding element attached to the pin.

18. The device according to claim 1, wherein the holding element has an independent clamping action so that the holding element is independently fixed in its position on the shaft of the pin.

19. The device according to claim 1, wherein the holding element is formed as a rubber ring, which in the attached position of the device is of larger size than the opening in the implant film.

20. The device according to claim 1, wherein the holding element is formed as a rubber ring which in an unstressed state has a smaller diameter than the shaft of the pin, so that the rubber ring exerts a compressive stress or compressive force when the rubber ring is mounted on the shaft of the pin.

21. The device according to claim 1, wherein the holding element is formed as a clamping spring, which has a pre-tensioning so that the holding element in the attached position of the device, on account of its pre-tensioning, is independently fixed on the shaft of the pin.

22. The device according to claim 1, wherein the holding element has conical dimensions that co-operate with a conical section on the shaft of the pin, in order to exert a pressure in the direction of the implant film in the attached state.

23. The device according to claim 1, further comprising a tool configured to place the holding element on the shaft of the pin, the tool including two hollow bodies guided within one another, the two hollow bodies including an inner tube and an outer tube which are movable relative to one another in the direction of their longitudinal axes between a first position and a second position.

24. The device according to claim 23, wherein in the first position the front side of the inner tube projects at least partly from the outer tube, and in the second position the inner tube is largely retracted into the outer tube.

25. The device according to claim 23, wherein in the second position the front side of the inner tube is flush with the outer tube, or the inner tube is retracted into the outer tube.

26. The device according to claim 23, wherein an actuating mechanism is provided on the side of the tool opposite the front side, by means of which the relative movement of the inner tube with respect to the outer tube can be implemented.

27. The device according to claim 23, wherein the actuating mechanism includes two gripping elements that are simply supported in a common end point and are in each case connected at their free end to the inner tube.

28. The device according to claim 27, wherein squeezing the gripping elements produces a displacement of the inner tube with respect to the outer tube, so that the front side of the inner tube is retracted into the outer tube.

29. The device according to claim 27, wherein a mechanical stop is provided that limits the movement of the actuating mechanism and/or of the gripping elements.

30. The device according to claim 27, wherein the mechanical stop is designed so that the gripping elements can be squeezed until the front side of the inner tube is completely retracted into the outer tube.

31. The device according to claim 27, wherein the inner tube in its relative movement with respect to the outer tube is guided on an axis that extends from the inner tube as far as the common end point of the gripping elements.

32. The device according to claim 27, wherein the gripping elements are held by a pre-tensioning in an open position, in which the front side of the inner tube projects from the outer tube.

33. An implant attaching device for attaching an implant in an eye of a human or mammal, wherein the implant includes an implant film for contacting living tissue or nerves in a visual system of the eye and the implant film comprises an opening, the implant attaching device comprising:

a pin configured to fix the implant attaching device to living tissue or nerves, wherein the pin comprises:

an elongated shaft having a rear part and a front part, the front part configured to be embedded in the living tissue or nerves, wherein the front part includes a barb configured to anchor the elongated shaft in the living tissue or nerves; and a holding element capable of being elastically widened in a width direction of the rear part, wherein the holding element is configured to be removably arranged on the rear part of the elongated shaft in an attached position, so that the holding element engages on the elongated shaft and removably holds the implant film of the implant in an attached state on the rear part of the elongated shaft of the pin, wherein the holding element, in the attached position, does not extend past an end of the rear part of the elongated shaft and exerts an elastic force directed towards an axial center of the pin, wherein dimensions of the rear part of the elongated shaft of the pin are such that the rear part of the elongated shaft of the pin can be inserted through the opening of the implant film after the front part is embedded in the living tissue or nerves, wherein the elongated shaft and the holding element are configured such that the implant film can be removed without extracting the elongated shaft from the living tissue or nerves.

34. The device according to claim 5, wherein in the attached state, the implant film is located between the collar and the holding element.

35. The device according to claim 33, wherein in the attached state, the implant film is located between a collar and the holding element, wherein the collar is positioned in middle region of the elongated shaft and has a diameter larger than a diameter of the elongated shaft.

\* \* \* \* \*